(12) United States Patent
Kuno

(10) Patent No.: US 11,898,881 B2
(45) Date of Patent: Feb. 13, 2024

(54) GAS SENSOR MANUFACTURING METHOD, GAS SENSOR, AND PROTECTIVE COVER

(71) Applicant: NGK INSULATORS, LTD., Aichi (JP)

(72) Inventor: Toshiaki Kuno, Nagoya (JP)

(73) Assignee: NGK INSULATORS, LTD., Nagoya (JP)

( * ) Notice: Subject to any disclaimer, the term of this patent is extended or adjusted under 35 U.S.C. 154(b) by 0 days.

(21) Appl. No.: 17/939,034

(22) Filed: Sep. 7, 2022

(65) Prior Publication Data

US 2023/0075427 A1   Mar. 9, 2023

(30) Foreign Application Priority Data

Sep. 8, 2021 (JP) .................................. 2021-146158

(51) Int. Cl.
*G01N 33/00* (2006.01)
*G01D 11/24* (2006.01)

(52) U.S. Cl.
CPC ....... *G01D 11/245* (2013.01); *G01N 33/0037* (2013.01)

(58) Field of Classification Search
CPC .......................... G01D 11/245; G01N 33/0037
See application file for complete search history.

(56) References Cited

U.S. PATENT DOCUMENTS

| 2006/0042946 A1* | 3/2006 | Tsukahara | .......... | G01N 27/4077 |
| | | | | 204/426 |
| 2016/0114420 A1* | 4/2016 | Makino | .................. | B23K 11/34 |
| | | | | 219/67 |
| 2017/0363599 A1* | 12/2017 | Adachi | .............. | G01N 33/0009 |
| 2021/0102928 A1* | 4/2021 | Adachi | .................. | G01D 11/26 |

FOREIGN PATENT DOCUMENTS

| JP | 06235714 A | * | 8/1994 |
| JP | 2007078473 A | * | 3/2007 |
| JP | 2019-158572 A | | 9/2019 |

* cited by examiner

*Primary Examiner* — Jamel E Williams
(74) *Attorney, Agent, or Firm* — Mattingly & Malur, PC

(57) ABSTRACT

In a method for manufacturing a gas sensor, a casing for holding a sensor element and a protective cover are connected to each other so that a distal end portion of the sensor element is covered with the protective cover. A first gas chamber, a sensor element chamber, and a second gas chamber into which gas is introduced from the outside are formed between the protective cover and the casing. In the gas introduction portion including the first gas chamber, the sensor element chamber, and the second gas chamber, there is no joint portion formed by welding.

13 Claims, 6 Drawing Sheets

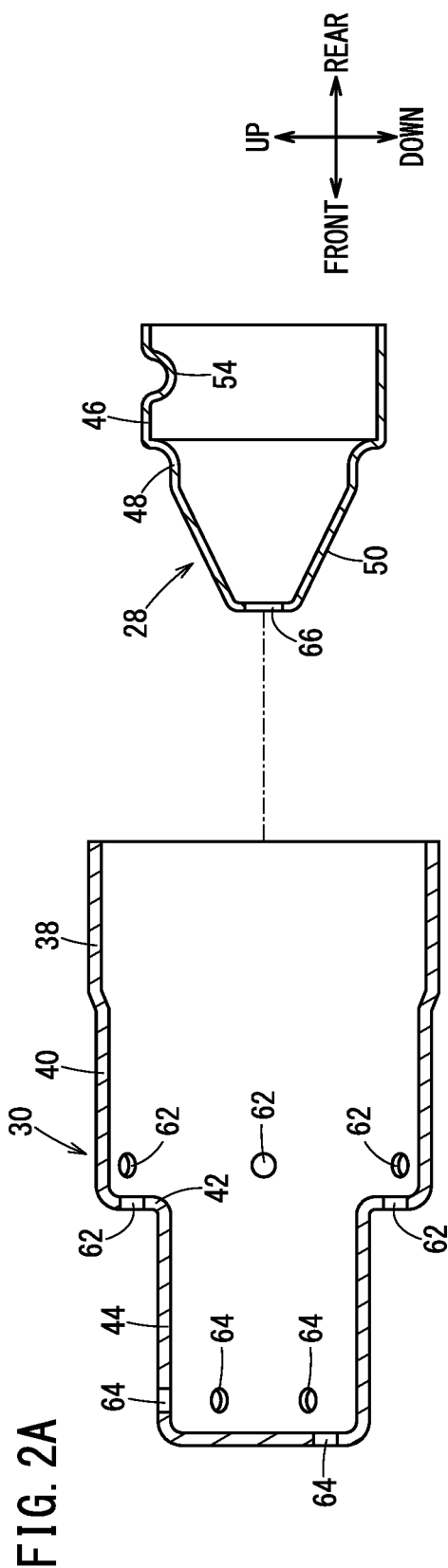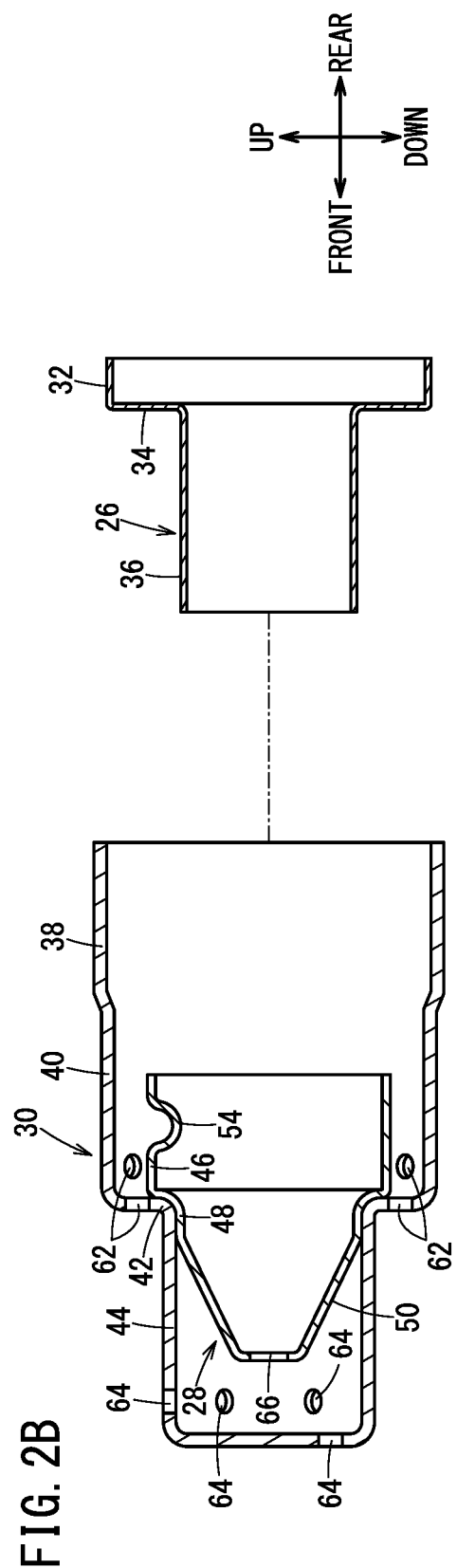

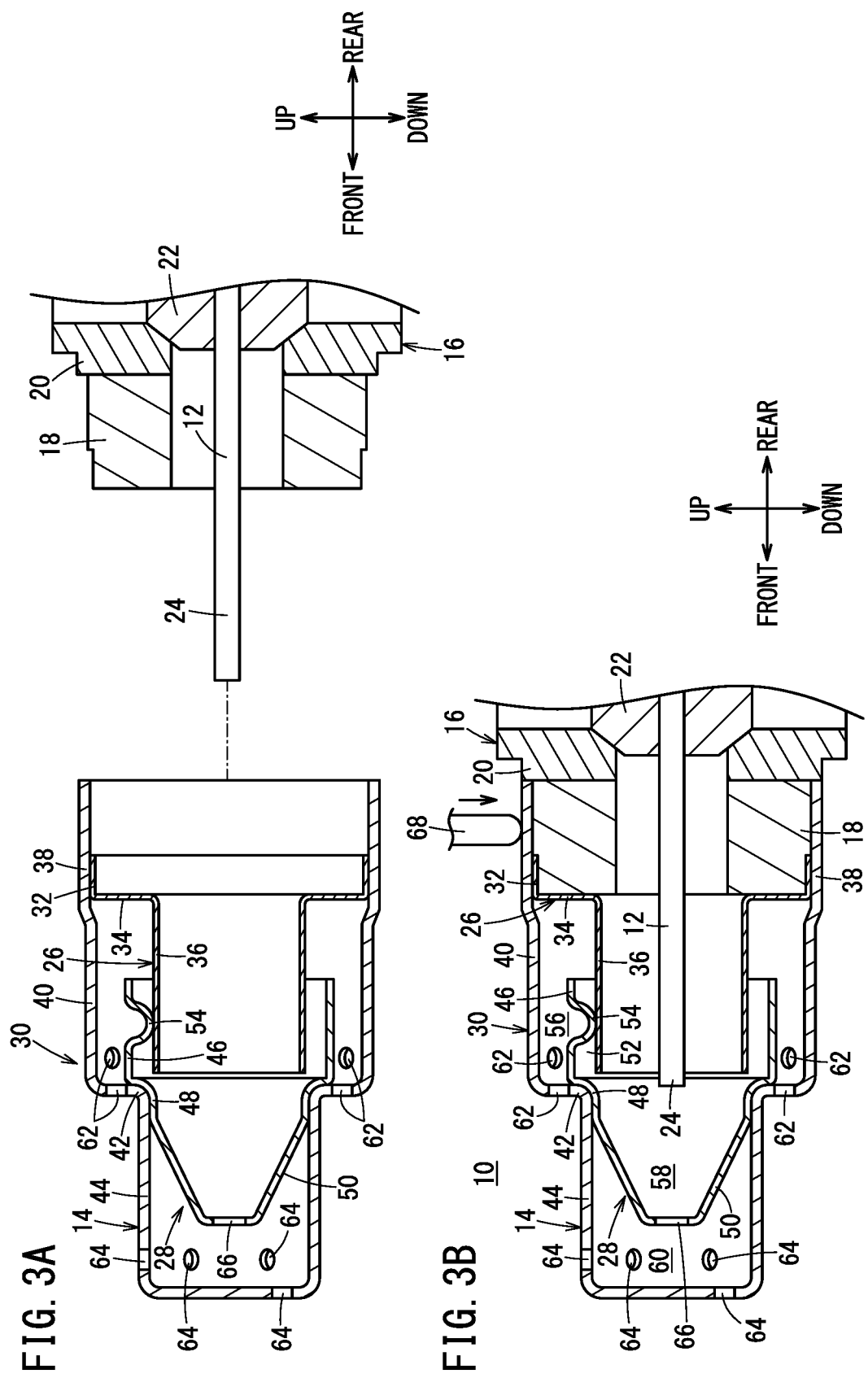

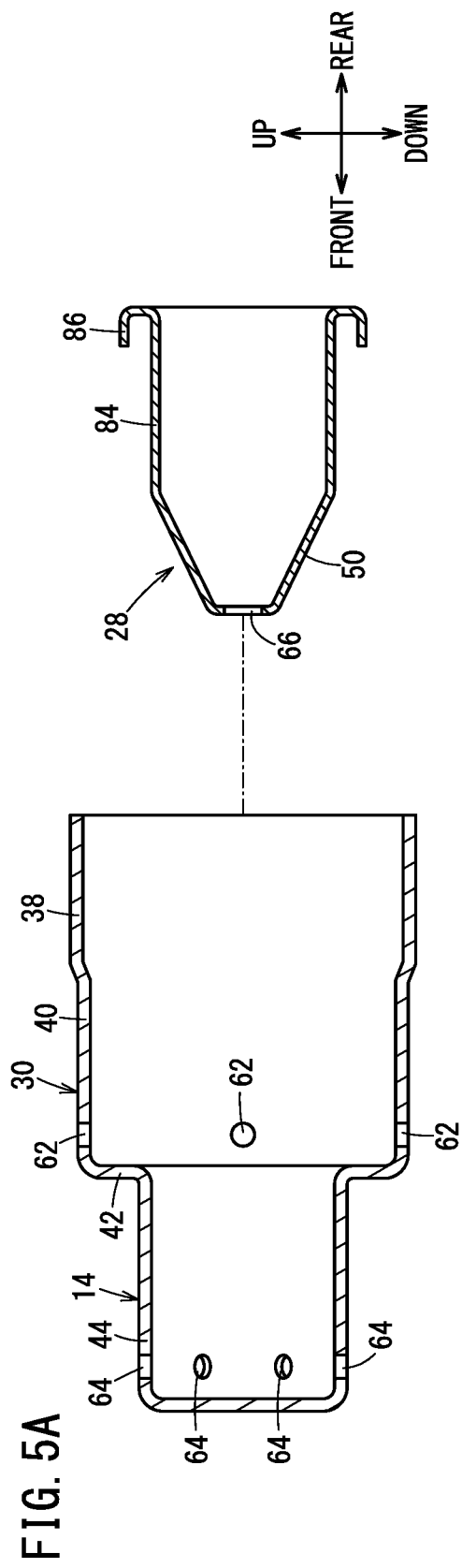
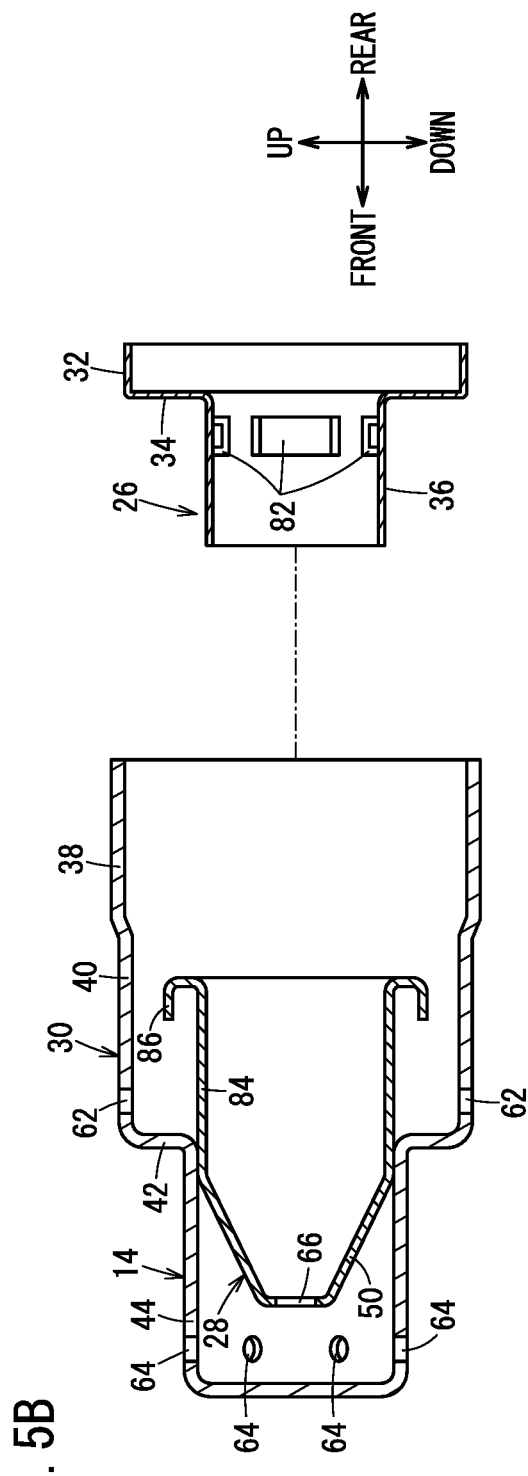
FIG. 5A
FIG. 5B

GAS SENSOR MANUFACTURING METHOD, GAS SENSOR, AND PROTECTIVE COVER

CROSS-REFERENCE TO RELATED APPLICATIONS

This application is based upon and claims the benefit of priority from Japanese Patent Application No. 2021-146158 filed on Sep. 8, 2021, the contents of which are incorporated herein by reference.

BACKGROUND OF THE INVENTION

Field of the Invention

The present invention relates to a gas sensor manufacturing method, a gas sensor, and a protective cover.

Description of the Related Art

The gas sensor measures the concentration of a predetermined gas component in a gas to be measured. The gas sensor includes a casing, a sensor element, and a protective cover. The casing holds the sensor element. The distal end portion of the sensor element protrudes from the distal end portion of the casing. The protective cover is connected to the casing so as to cover the distal end portion of the sensor element. The protective cover includes an inner member and an outer member. The inner member is connected to the distal end portion of the casing so as to surround the distal end portion of the sensor element. The inner member is fixed to the distal end portion of the casing by welding. The outer member is connected to the casing so as to cover the inner member and the distal end portion of the sensor element. A connection portion between the outer member and the casing is fixed by welding. JP 2019-158572 A discloses that a connection portion between a protective cover and a casing is fixed by spot welding.

SUMMARY OF THE INVENTION

When the inner member and the distal end portion of the casing are welded, fumes are generated. The fumes scatter and adhere to the inner member and the casing. When the fumes adhere to the connection portion between the outer member and the casing, the accuracy of connecting the outer member and the casing is reduced. In addition, the distal end portion of the sensor element is disposed in a space surrounded by the protective cover and the casing. Gas flows into this space from the outside. When the fumes adhere to the inner member, the flow of the gas is hindered. This reduces the measurement accuracy of the sensor element. Thus, adhesion of fumes increases the failure rate of the gas sensor. In addition, since the inner member and the distal end portion of the casing are welded to each other, a manufacturing cost is increased. Further, since the adhesion of fumes is monitored, the number of management man-hours required for manufacturing the gas sensor is increased.

An object of the present invention is to solve the above-described problems.

According to a first aspect of the present invention, provided is a method for manufacturing a gas sensor including a casing, a sensor element held by the casing, and a protective cover configured to protect a distal end portion of the sensor element that protrudes from the casing, the method comprising: connecting the casing and the protective cover to each other in a manner so that the distal end portion of the sensor element is covered with the protective cover, wherein a gas is introduced from outside into a space surrounded by the protective cover and the casing, and a region of the protective cover and a region of the casing that define the space include no joint portion formed by welding.

According to a second aspect of the present invention, provided is a gas sensor comprising: a casing; a sensor element held by the casing; and a protective cover configured to protect a distal end portion of the sensor element that protrudes from the casing, wherein the distal end portion of the sensor element is covered with the protective cover by connecting the casing and the protective cover to each other, a gas is introduced from outside into a space surrounded by the protective cover and the casing, and a region of the protective cover and a region of the casing that define the space include no joint portion formed by welding.

According to a third aspect of the present invention, provided is a protective cover that protects a distal end portion of a sensor element held by a casing, the protective cover comprising: an inner member disposed in the casing so as to surround the distal end portion of the sensor element; and an outer member disposed in the casing so as to cover the distal end portion of the sensor element and the inner member, wherein the inner member and the outer member are connected by being fitted to each other.

According to the present invention, fumes do not adhere to the protective cover and the casing. Thus, the accuracy of connecting the protective cover and the casing is improved. In addition, gas smoothly flows through the space surrounded by the protective cover and the casing. This improves the measurement accuracy of the sensor element. Therefore, in the present invention, the failure rate of the gas sensor is suppressed. In addition, the manufacturing cost of the gas sensor can be reduced. Further, it is possible to reduce management man-hours required for manufacturing the gas sensor.

The above and other objects, features, and advantages of the present invention will become more apparent from the following description when taken in conjunction with the accompanying drawings, in which a preferred embodiment of the present invention is shown by way of illustrative example.

BRIEF DESCRIPTION OF THE DRAWINGS

FIG. 2A is a cross-sectional view showing fitting between an outer member and an intermediate member;

FIG. 2B is a cross-sectional view showing fitting of an inner member to the outer member and the intermediate member;

FIG. 3A is a cross-sectional view showing connection between a protective cover and a casing;

FIG. 3B is a cross-sectional view showing spot-welding at a connection portion between the outer member and the casing;

FIG. 5A is a cross-sectional view showing fitting between the outer member and the intermediate member;

FIG. 5B is a cross-sectional view showing fitting of the inner member to the outer member and the intermediate member;

DESCRIPTION OF THE INVENTION

Figure 1:
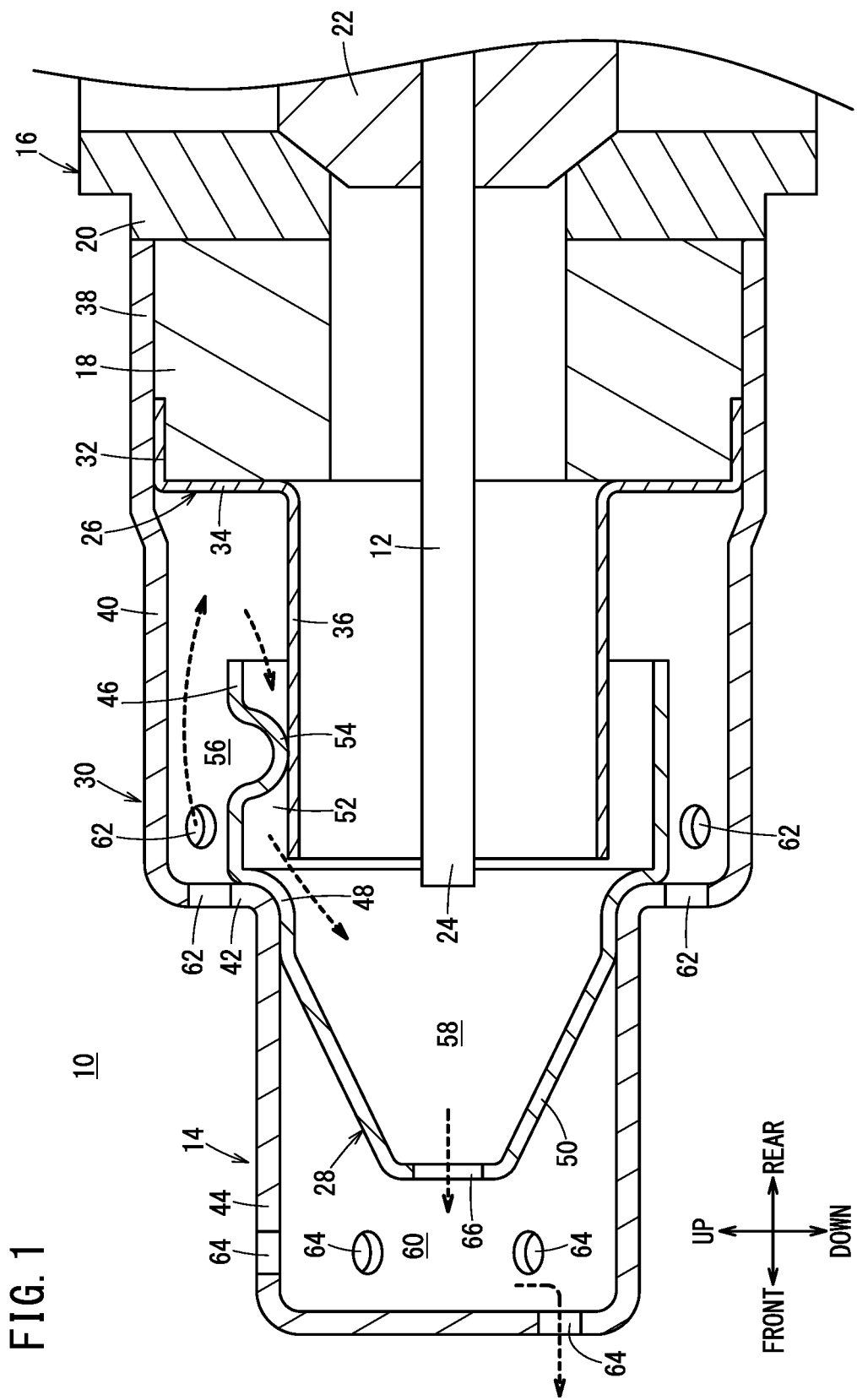
FIG. 1 is a cross-sectional view of a gas sensor according to an embodiment.

FIG. 1 is a cross-sectional view of a gas sensor 10 manufactured by a gas sensor manufacturing method according to the present embodiment. The gas sensor 10 is installed in, for example, an exhaust pipe connected to an engine of a vehicle (not shown). The gas sensor 10 detects the concentration of a gas component such as NOx contained in a gas to be measured (exhaust gas) discharged from the engine.

The gas sensor 10 includes a sensor element 12, a protective cover 14, and a casing 16. The sensor element 12 detects the concentration of a predetermined gas component in the gas to be measured. The casing 16 holds the sensor element 12. The casing 16 is a cylinder made of metal. Specifically, the casing 16 includes a housing 18, a fixing member 20, and a sensor support portion 22. The fixing member 20 is a cylindrical member made of metal. The fixing member 20 is connected to the pipe by welding, screwing, or the like. The housing 18 is a cylindrical member made of metal. The housing 18 is fixed to one surface (a surface close to the protective cover 14) of the fixing member 20. The sensor support portion 22 is fixed to the other surface of the fixing member 20. The housing 18, the fixing member 20, and the sensor support portion 22 are connected substantially coaxially. Note that the phrase "substantially coaxial" includes both a case where a plurality of objects are coaxial with each other and a case where the plurality of objects are slightly deviated from the coaxial state.

The sensor element 12 has an elongated plate shape. In the following description, the longitudinal direction of the sensor element 12 (the left-right direction in FIG. 1) is referred to as a front-rear direction. The thickness direction of the sensor element 12 (the up-down direction in FIG. 1) is referred to as an up-down direction. The width direction of the sensor element 12 (a direction perpendicular to the left-right direction and the up-down direction in FIG. 1) is referred to as a left-right direction. In addition, in the following description, a front end portion of the sensor element 12 or the like is referred to as a distal end portion. Further, a rear end portion of the sensor element 12 or the like is referred to as a base end portion.

The sensor element 12 is held by the casing 16 substantially coaxially with the casing 16. That is, the sensor support portion 22 substantially coaxially supports the base end portion of the sensor element 12. The sensor element 12 extends forward from the sensor support portion 22 and passes through the fixing member 20 and the housing 18. Accordingly, a distal end portion 24 of the sensor element 12 protrudes forward from the housing 18.

The protective cover 14 is a bottomed cylinder made of metal. The protective cover 14 is connected to a side surface (outer peripheral surface) of the housing 18 so as to cover the distal end portion 24 of the sensor element 12 and the housing 18. The protective cover 14 is connected to the housing 18 substantially coaxially with the sensor element 12 and the casing 16.

Specifically, the protective cover 14 includes an inner member 26, an intermediate member 28, and an outer member 30.

The inner member 26 is a stepped cylindrical member made of metal. The inner member 26 is connected to the housing 18 substantially coaxially with the sensor element 12 and the housing 18. The inner member 26 includes a large-diameter portion 32, a step portion 34, and a small-diameter portion 36. The large-diameter portion 32 is a cylindrical portion fitted to the side surface of the housing 18. The small-diameter portion 36 is a cylindrical portion having a smaller diameter than the large-diameter portion 32. The small-diameter portion 36 is a cylindrical portion having a larger diameter than the sensor element 12. The small-diameter portion 36 extends forward from the distal end portion of the housing 18. The small-diameter portion 36 extends substantially parallel to the sensor element 12. Accordingly, the small-diameter portion 36 is disposed so as to surround the distal end portion 24 of the sensor element 12. The step portion 34 connects the large-diameter portion 32 and the small-diameter portion 36. The step portion 34 extends along the distal end portion of the housing 18. Incidentally, the distal end of the sensor element 12 slightly protrudes from the distal end portion of the small-diameter portion 36.

The outer member 30 is a stepped member made of metal. Further, the outer member 30 is a bottomed cylindrical member. The outer member 30 is connected to the housing 18 substantially coaxially with the sensor element 12 and the housing 18. The outer member 30 includes a large-diameter portion 38, a body portion 40, a step portion 42, and a small-diameter portion 44. The large-diameter portion 38 is a cylindrical portion fitted to the side surface of the housing 18. The large-diameter portion 38 is fitted to the side surface of the housing 18 by press-fitting the outer member 30 onto the housing 18. The large-diameter portion 32 of the inner member 26 is fitted to the inner surface (inner peripheral surface) of the large-diameter portion 38 by press-fitting the inner member 26 into the outer member 30.

Further, the fitting portion between the large-diameter portion 38 and the side surface of the housing 18 is fixed by spot welding, for example. The spot welding is performed at intervals of a predetermined angle in the circumferential direction of the outer member 30. The spot welding includes various types of spot welding such as resistance spot welding and laser spot welding. Further, in the present embodiment, the fitting portion between the large-diameter portion 38 and the side surface of the housing 18 may be fixed by various types of welding. The various types of welding include resistance welding including resistance spot welding, and laser welding including laser spot welding. Furthermore, even if fumes generated by welding adhere to the fitting portion between the large-diameter portion 38 and the side surface of the housing 18, the fitting portion is not affected by the fumes. This is because a gas flow path does not exist in the vicinity of this fitting portion.

The body portion 40 extends forward from the large-diameter portion 38. The body portion 40 extends substantially parallel to the sensor element 12 and the small-diameter portion 36 of the inner member 26. Accordingly, the body portion 40 is disposed so as to surround the distal end portion 24 of the sensor element 12 and the inner member 26. The step portion 42 is provided forward of the body portion 40. The step portion 42 is connected to the small-diameter portion 44. The small-diameter portion 44 is a cylindrical portion having a smaller diameter than the large-diameter portion 38 and the body portion 40. The small-diameter portion 44 is a cylindrical portion having a larger diameter than the small-diameter portion 36 of the inner member 26. The small-diameter portion 44 is a bottomed cylinder that covers the distal end portion 24 of the sensor element 12.

The intermediate member 28 is disposed between the inner member 26 and the outer member 30. The intermediate member 28 is a bottomed cylindrical member made of metal. The intermediate member 28 includes a tubular portion 46, an intermediate portion 48, and a truncated conical portion 50. The tubular portion 46 is a cylindrical portion having a larger diameter than the small-diameter portion 36 of the inner member 26. The tubular portion 46 is a cylindrical portion having a smaller diameter than the body portion 40. A gap 52 is formed between the tubular portion 46 and the small-diameter portion 36 of the inner member 26. A plurality of protruding portions 54 that protrude radially inward are formed on the tubular portion 46. Each protruding portion 54 comes into contact with a side surface (outer peripheral surface) of the small-diameter portion 36 of the inner member 26. That is, by press-fitting the inner member 26 into the intermediate member 28, the small-diameter portion 36 comes into contact with the plurality of protruding portions 54, whereby the inner member 26 is fitted to an inner surface of the tubular portion 46. In FIG. 1, only one protruding portion 54 is shown. The intermediate portion 48 connects the tubular portion 46 and the truncated conical portion 50. By press-fitting the intermediate member 28 into the outer member 30, the intermediate portion 48 is connected to an inner surface of the step portion 42 of the outer member 30. The truncated conical portion 50 is connected to the intermediate portion 48. The truncated conical portion 50 is disposed between the distal end portion 24 of the sensor element 12 and the small-diameter portion 44 of the outer member 30.

A space surrounded by the inner member 26 and the outer member 30 is formed as a first gas chamber 56. A space surrounded by the intermediate member 28 and the inner member 26 is formed as a sensor element chamber 58. A space surrounded by the intermediate member 28 and the outer member 30 is formed as a second gas chamber 60. A plurality of first communication holes 62 are formed in the body portion 40 and the step portion 42 of the outer member 30. Each of the plurality of first communication holes 62 allows the exhaust pipe and the first gas chamber 56 to communicate with each other. The first communication holes 62 are formed at intervals of a predetermined angle in the circumferential direction of the outer member 30. A plurality of second communication holes 64 are formed in the small-diameter portion 44 of the outer member 30. Each of the plurality of second communication holes 64 allows the exhaust pipe and the second gas chamber 60 to communicate with each other. The second communication holes 64 are formed at intervals of a predetermined angle in the circumferential direction of the outer member 30. A gas outlet 66 is formed in the truncated conical portion 50 of the intermediate member 28. The gas outlet 66 allows the sensor element chamber 58 and the second gas chamber 60 to communicate with each other.

The gas to be measured flows from the first communication holes 62 into the first gas chamber 56 as indicated by dashed arrows. The gas to be measured in the first gas chamber 56 flows into the sensor element chamber 58 through the gap 52. The gas to be measured in the sensor element chamber 58 flows to the outside through the gas outlet 66, the second gas chamber 60, and the second communication holes 64. The distal end portion 24 of the sensor element 12 extends into the sensor element chamber 58. Therefore, when the gas to be measured temporarily stays in the sensor element chamber 58, part of the gas to be measured is taken into the sensor element 12. Thus, the sensor element 12 can measure the concentration of a predetermined gas component in the gas to be measured.

Next, the manufacturing method of the present embodiment will be described with reference to FIGS. 2A to 3B.

First, as shown in FIG. 2A, in a state where an inner surface of the outer member 30 and the truncated conical portion 50 of the intermediate member 28 are opposed to each other, the intermediate portion 48 of the intermediate member 28 is press-fitted to the step portion 42 of the outer member 30. Thus, as shown in FIG. 2B, the intermediate member 28 is substantially coaxially fitted to the inner surface of the outer member 30.

Next, in a state where an inner surface of the intermediate member 28 and the small-diameter portion 36 of the inner member 26 are opposed to each other, the small-diameter portion 36 of the inner member 26 is press-fitted to the protruding portions 54 of the intermediate member 28. Thus, as shown in FIG. 3A, the inner member 26 is substantially coaxially fitted to the inner surface of the intermediate member 28. As a result, the protective cover 14 having a bottomed cylindrical shape is formed. Therefore, each step in FIGS. 2A and 2B corresponds to an assembly step for forming the protective cover 14. As described above, in the protective cover 14, the outer member 30, the intermediate member 28, and the inner member 26 are integrally connected in this order by press fitting. In other words, the protective cover 14 has no joint portion formed by welding.

Next, as shown in FIG. 3A, in a state where the distal end portion 24 of the sensor element 12 held by the casing 16 and the inner member 26 of the protective cover 14 are opposed to each other, the large-diameter portion 38 of the outer member 30 is press-fitted onto the side surface of the housing 18 of the casing 16. Thus, as shown in FIG. 3B, an inner surface of the large-diameter portion 38 and the side surface of the housing 18 are fitted to each other, and an inner surface of the large-diameter portion 32 of the inner member 26 and the side surface of the housing 18 are fitted to each other. As a result, the protective cover 14 is connected to the casing 16 substantially coaxially with the sensor element 12 and the casing 16. Moreover, the inner member 26 is disposed so as to surround the distal end portion 24 of the sensor element 12. Further, the intermediate member 28 is disposed so as to cover the distal end portion 24 of the sensor element 12 and the small-diameter portion 36 of the inner member 26. Furthermore, the outer member 30 is disposed so as to cover the distal end portion 24 of the sensor element 12, the inner member 26, and the intermediate member 28. In addition, the first gas chamber 56, the second gas chamber 60, and the sensor element chamber 58 are formed. Since the protective cover 14 and the casing 16 are connected to each other, no joint portion formed by welding exists in the protective cover 14 and the casing 16.

Next, spot welding is performed on a connection portion between the large-diameter portion 38 of the outer member 30 and the side surface of the housing 18. At this time, a jig 68 for spot welding is brought into contact with the large-diameter portion 38, and the large-diameter portion 38 and the housing 18 are energized to join the large-diameter portion 38 and the housing 18. The spot welding is performed at a plurality of locations at intervals of a predetermined angle in the circumferential direction of the large-diameter portion 38. Thus, the protective cover 14 is fixed to the casing 16. As a result, the gas sensor 10 is completed. Therefore, each step in FIGS. 3A and 3B corresponds to a connecting step for connecting the protective cover 14 and the casing 16.

Next, a modification of the present embodiment will be described with reference to FIGS. 4 to 6B. The same components as those described with reference to FIGS. 1 to 3B are denoted by the same reference numerals.

Figure 4:
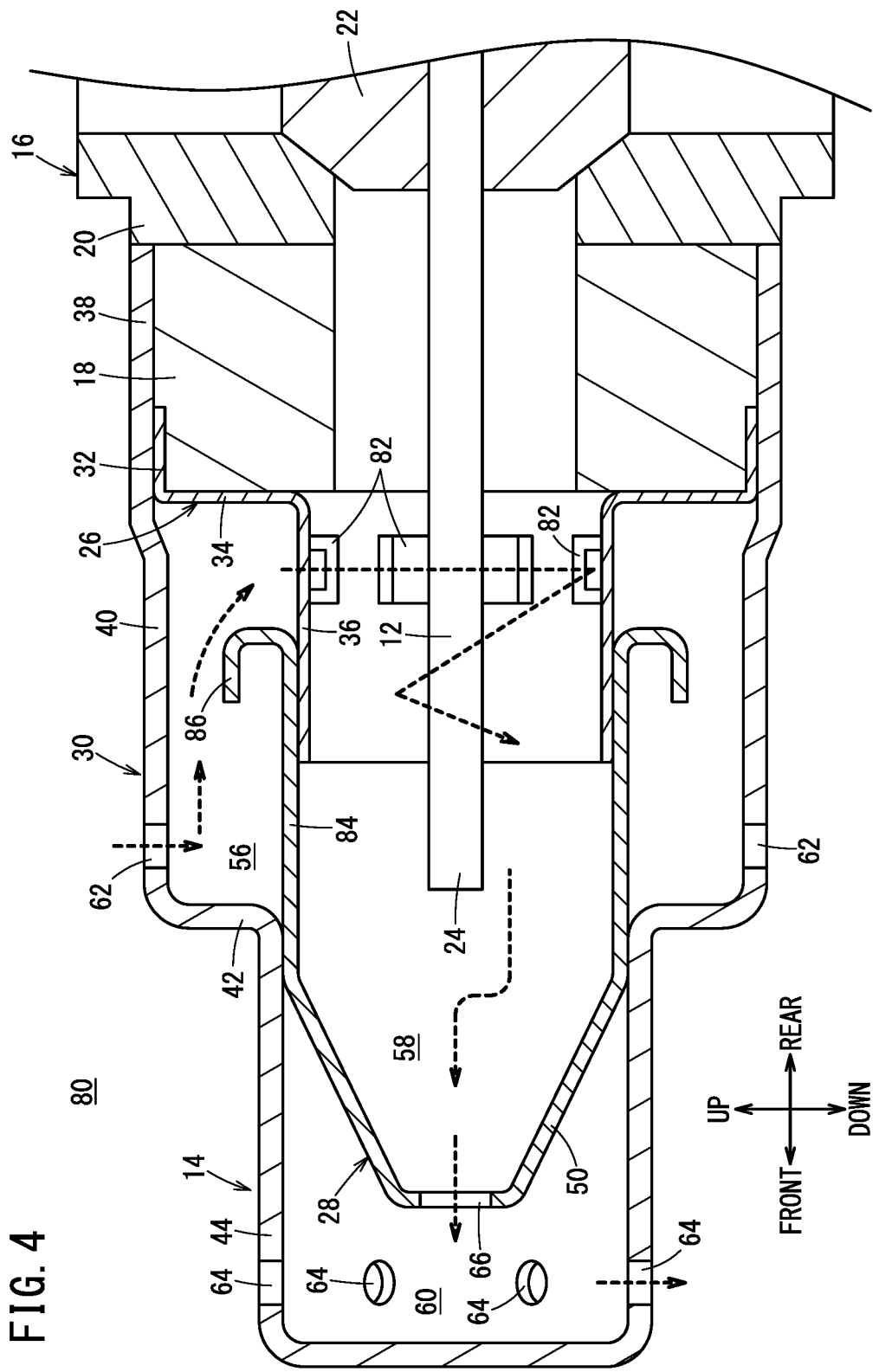
FIG. 4 is a cross-sectional view showing a gas sensor according to a modification.

FIG. 4 is a cross-sectional view of a gas sensor 80 according to the modification. This gas sensor 80 is different from the gas sensor 10 shown in FIG. 1 in that the gap 52 is not formed. Further, in the gas sensor 80, a plurality of through holes 82 are formed in the inner member 26. The plurality of through holes 82 are formed in the inner member 26, at locations near the housing 18. The gas to be measured flows from the first gas chamber 56 into the sensor element chamber 58 via the plurality of through holes 82, as indicated by dashed arrows.

Further, the gas sensor 80 of the modification is different from the gas sensor 10 shown in FIG. 1 in the shape of the intermediate member 28. Specifically, the intermediate member 28 includes a cylindrical portion 84, the truncated conical portion 50, and a diffusion portion 86. The cylindrical portion 84 has a diameter larger than the small-diameter portion 36 of the inner member 26 and smaller than the small-diameter portion 44 of the outer member 30. The distal end portion of the cylindrical portion 84 is fitted to an inner surface of the small-diameter portion 44 of the outer member 30 by press-fitting the intermediate member 28 into the outer member 30. Further, the small-diameter portion 36 of the inner member 26 is fitted to the inner surface of the cylindrical portion 84 by press-fitting the inner member 26 into the intermediate member 28. The truncated conical portion 50 extends forward from the cylindrical portion 84.

The diffusion portion 86 is formed to have a substantially U-shaped cross section at the rear end portion (base end portion) of the cylindrical portion 84. That is, the diffusion portion 86 is formed by curving the base end portion of the cylindrical portion 84 outward in the radial direction and folding it forward. The diffusion portion 86 prevents liquid such as water entering the first gas chamber 56 from passing through the plurality of through holes 82. Further, the diffusion portion 86 diffuses the gas to be measured that has entered the gap between the outer member 30 and the inner member 26 in the first gas chamber 56. Thus, the gas to be measured is guided to the plurality of through holes 82 of the first gas chamber 56.

Next, a manufacturing method according to a modification will be described with reference to FIGS. 5A to 6B.

First, as shown in FIG. 5A, in a state in which the inner surface of the outer member 30 and the truncated conical portion 50 of the intermediate member 28 are opposed to each other, the cylindrical portion 84 of the intermediate member 28 is press-fitted into the small-diameter portion 44 of the outer member 30. Thus, as shown in FIG. 5B, the intermediate member 28 is substantially coaxially fitted to the inner surface of the outer member 30.

Figure 6A:
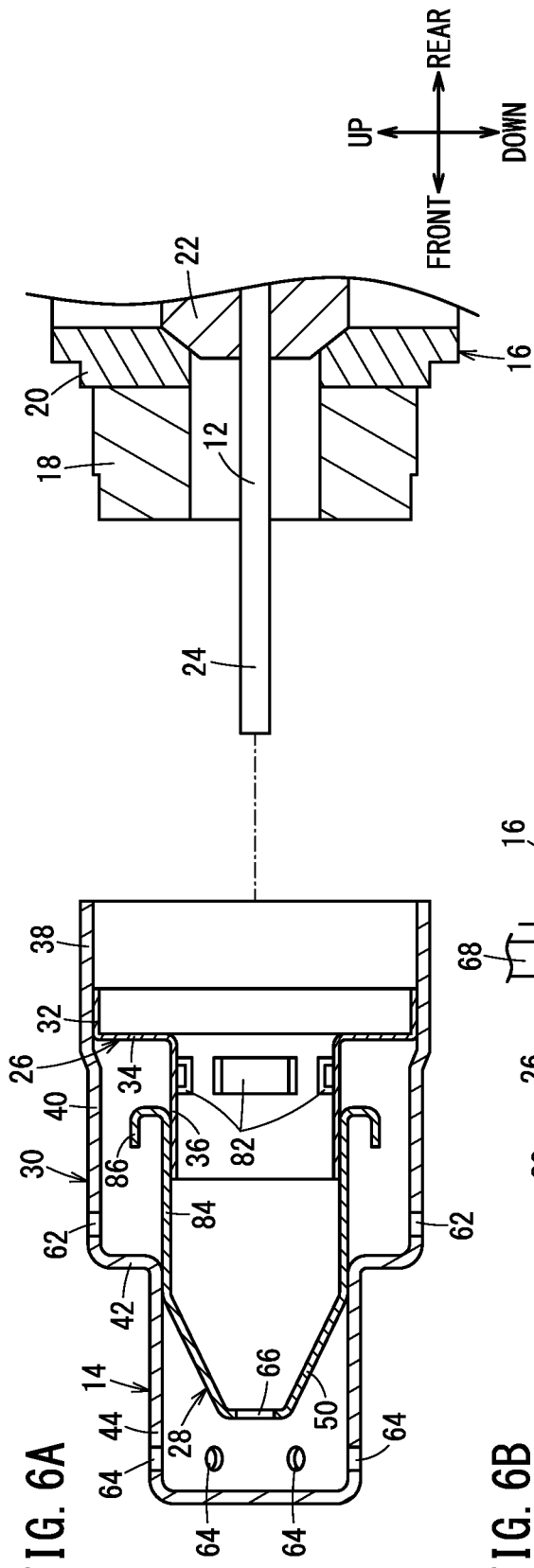
FIG. 6A is a cross-sectional view showing connection between the protective cover and the casing.

Next, in a state where the inner surface of the intermediate member 28 and the small-diameter portion 36 of the inner member 26 are opposed to each other, the small-diameter portion 36 of the inner member 26 is press-fitted into the cylindrical portion 84 of the intermediate member 28. Thus, as shown in FIG. 6A, the inner member 26 is substantially coaxially fitted to the inner surface of the intermediate member 28. As a result, the protective cover 14 having a bottomed cylindrical shape is formed. Therefore, each step in FIGS. 5A and 5B corresponds to an assembly step for forming the protective cover 14. In the protective cover 14, the outer member 30, the intermediate member 28, and the inner member 26 are integrally connected in this order by press fitting. In other words, the protective cover 14 has no joint portion formed by welding.

Figure 6B:
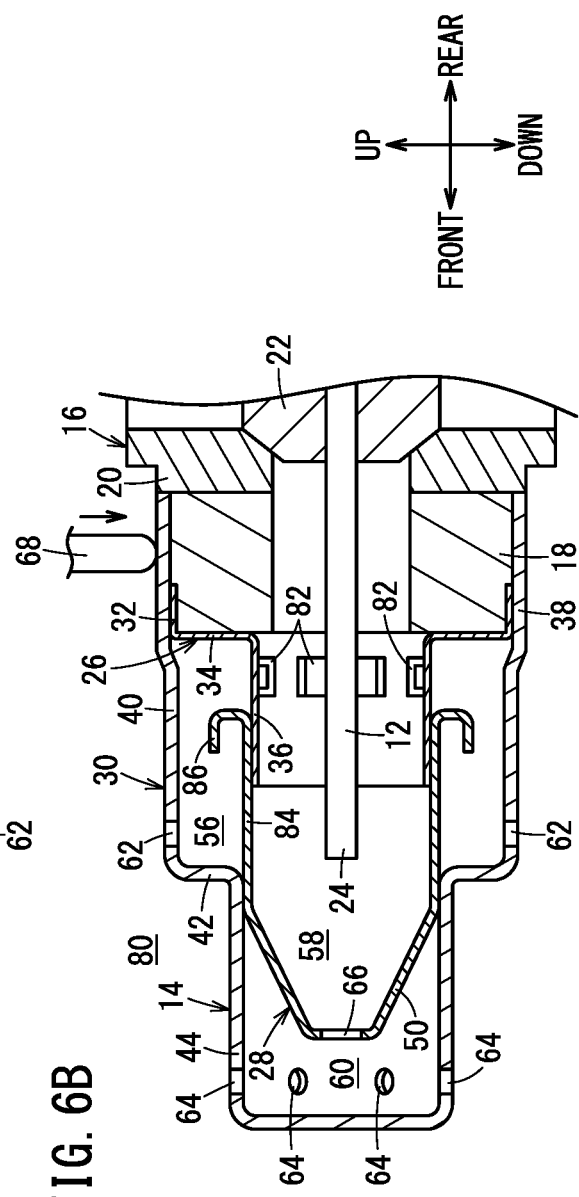
FIG. 6B is a cross-sectional view showing spot-welding at a connection portion between the outer member and the casing.

Next, as shown in FIG. 6A, in a state where the distal end portion 24 of the sensor element 12 held by the casing 16 and the inner member 26 of the protective cover 14 are opposed to each other, the large-diameter portion 38 of the outer member 30 is press-fitted onto the side surface of the housing 18 of the casing 16. Thus, as shown in FIG. 6B, the inner surface of the large-diameter portion 38 and the side surface of the housing 18 are fitted to each other, and the inner surface of the large-diameter portion 32 of the inner member 26 and the side surface of the housing 18 are fitted to each other. As a result, the protective cover 14 is connected to the casing 16 substantially coaxially with the sensor element 12 and the casing 16. Moreover, the inner member 26 is disposed so as to surround the distal end portion 24 of the sensor element 12. Further, the intermediate member 28 is disposed so as to cover the distal end portion 24 of the sensor element 12 and the small-diameter portion 36 of the inner member 26. Furthermore, the outer member 30 is disposed so as to cover the distal end portion 24 of the sensor element 12, the inner member 26, and the intermediate member 28. In addition, the first gas chamber 56, the second gas chamber 60, and the sensor element chamber 58 are formed. Therefore, according to the modification as well, no joint portion formed by welding exists in the protective cover 14 and the casing 16.

Next, spot welding is performed on a connection portion between the large-diameter portion 38 of the outer member 30 and the side surface of the housing 18. The spot welding is performed at a plurality of locations at intervals of a predetermined angle in the circumferential direction of the large-diameter portion 38. Thus, the protective cover 14 is fixed to the casing 16. As a result, the gas sensor 80 is completed. Therefore, each step in FIGS. 6A and 6B corresponds to a connecting step for connecting the protective cover 14 and the casing 16.

It should be noted that the case where the protective cover 14 and the casing 16 are fitted to each other by press fitting has been described with reference to FIGS. 1 to 6B. However, in the present embodiment, the protective cover and the casing may be connected to each other by any method. For example, a groove may be formed in one of the protective cover and the casing, and a protrusion may be formed in the other. The protective cover and the casing are connected to each other by the protrusion being fitted into the groove.

The invention that can be grasped from the above-described embodiment and modification will be described below.

According to a first aspect of the present invention, provided is a method for manufacturing a gas sensor (10, 80) including a casing (16), a sensor element (12) held by the casing (16), and a protective cover (14) configured to protect a distal end portion (24) of the sensor element (12) that protrudes from the casing (16), the method comprising: a connecting step of connecting the casing (16) and the protective cover (14) to each other in a manner so that the distal end portion (24) of the sensor element (12) is covered with the protective cover (14), wherein a gas is introduced from outside into a space (56, 58, 60) surrounded by the protective cover (14) and the casing (16), and a region of the protective cover (14) and a region of the casing (16) that define the space (56, 58, 60) include no joint portion formed by welding.

According to the present invention, fumes do not adhere to the protective cover (14) and the casing (16). Thus, the accuracy of connecting the protective cover (14) and the casing (16) can be ensured. Further, gas smoothly flows into the space (56, 58, 60) surrounded by the protective cover (14) and the casing (16). This makes it possible to suppress a decrease in the measurement accuracy of the sensor element (12). Therefore, according to the present invention, the failure rate of the gas sensor (10, 80) can be suppressed. In addition, the manufacturing cost of the gas sensor (10, 80) can be reduced. Furthermore, it is possible to reduce management man-hours required for manufacturing the gas sensor (10, 80).

In the first aspect of the present invention, in the connecting step, the protective cover (14) and the casing (16) are fitted to each other.

As a result, the above-described effects can be easily obtained.

In the first aspect of the present invention, in the connecting step, the protective cover (14) and the casing (16) are fitted to each other by press fitting.

As a result, the above-described effects can be easily obtained.

In the first aspect of the present invention, the protective cover (14) includes an inner member (26) disposed in the casing (16) so as to surround the distal end portion (24) of the sensor element (12), and an outer member (30) disposed in the casing (16) so as to cover the distal end portion (24) of the sensor element (12) and the inner member (26), the method further comprises, prior to the connecting step, an assembly step of forming the protective cover (14) by fitting the inner member (26) and the outer member (30) to each other by press fitting, and in the connecting step, the outer member (30) and a side surface of the casing (16) are connected to each other, and the inner member (26) and the side surface of the casing (16) are connected to each other.

Since welding is not performed in the assembly step, the number of manufacturing steps can be reduced. Thus, the cost of the gas sensor (10, 80) can be reduced. Moreover, the accuracy of combination of the inner member (26) and the outer member (30) is improved. Further, the accuracy of combination of the protective cover (14) and the casing (16) is improved. Furthermore, it is possible to prevent a decrease in the measurement accuracy of the sensor element (12) due to adhesion of fumes.

In the first aspect of the present invention, the protective cover (14) further includes an intermediate member (28) disposed between the inner member (26) and the outer member (30) and configured to cover the distal end portion (24) of the sensor element (12), and in the assembly step, the intermediate member (28) is fitted to an inner surface of the outer member (30) by press fitting, and thereafter, the inner member (26) is fitted to the inner surface of the outer member (30) and an inner surface of the intermediate member (28) by press fitting.

As a result, the above-described effects can be easily obtained.

In the first aspect of the present invention, the outer member (30), the intermediate member (28), and the inner member (26) are substantially coaxially fitted to each other, and in the connecting step, the casing (16) and the protective cover (14) are connected to each other in a manner so that the sensor element (12), the casing (16), and the protective cover (14) are substantially coaxial with each other.

As a result, the accuracy of combination of the components constituting the gas sensor (10, 80) and the measurement accuracy of the sensor element (12) are improved.

In the first aspect of the present invention, in the connecting step, a connection portion between the outer member (30) and the side surface of the casing (16) is fixed by welding.

Since welding is performed after the protective cover (14) is attached to the casing (16), it is possible to prevent fumes from entering.

In the first aspect of the present invention, in the connecting step, the connection portion between the outer member (30) and the side surface of the casing (16) is fixed by resistance welding.

As a result, the protective cover (14) can be fixed to the casing (16) at low cost.

In the first aspect of the present invention, in the connecting step, the connection portion between the outer member (30) and the side surface of the casing (16) is fixed by laser welding.

As a result, the protective cover (14) can be accurately fixed to the casing (16) in a short time.

In the first aspect of the present invention, in the connecting step, the connection portion between the outer member (30) and the side surface of the casing (16) is fixed by spot welding.

As a result, the protective cover (14) can be fixed to the casing (16) at a lower cost.

According to a second aspect of the present invention, provided is a gas sensor (10, 80) comprising: a casing (16); a sensor element (12) held by the casing (16); and a protective cover (14) configured to protect a distal end portion (24) of the sensor element (12) that protrudes from the casing (16), wherein the distal end portion (24) of the sensor element (12) is covered with the protective cover (14) by connecting the casing (16) and the protective cover (14) to each other, a gas is introduced from outside into a space (56, 58, 60) surrounded by the protective cover (14) and the casing (16), and a region of the protective cover (14) and a region of the casing (16) that define the space (56, 58, 60) include no joint portion formed by welding.

Also according to the present invention, fumes do not adhere to the protective cover (14) and the casing (16). Thus, the accuracy of connecting the protective cover (14) and the casing (16) can be ensured. Further, gas smoothly flows into the space (56, 58, 60) surrounded by the protective cover (14) and the casing (16). This makes it possible to suppress a decrease in the measurement accuracy of the sensor element (12). Therefore, in the present invention, the failure rate of the gas sensor (10, 80) can be suppressed. In addition, the manufacturing cost of the gas sensor (10, 80) can be reduced. Furthermore, it is possible to reduce management man-hours required for manufacturing the gas sensor (10, 80).

According to a third aspect of the present invention, provided is a protective cover (14) that protects a distal end portion (24) of a sensor element (12) held by a casing (16), the protective cover (14) comprising: an inner member (26) disposed in the casing (16) so as to surround the distal end portion (24) of the sensor element (12); and an outer member (30) disposed in the casing (16) so as to cover the distal end portion (24) of the sensor element (12) and the inner member (26), wherein the inner member (26) and the outer member (30) are connected by being fitted to each other.

Also according to the present invention, fumes do not adhere to the protective cover (14) and the casing (16). Thus, the accuracy of connecting the protective cover (14) and the casing (16) can be ensured. As a result, gas smoothly flows into the space (56, 58, 60) surrounded by the protective cover (14) and the casing (16). Therefore, it is possible to suppress a decrease in the measurement accuracy of the sensor element (12). Further, the failure rate of the gas sensor (10, 80) can be suppressed. Furthermore, it is possible to reduce management man-hours required for manufacturing the gas sensor (10, 80). In addition, since welding is not performed, the number of manufacturing steps can be reduced. As a result, the cost of the gas sensor (10, 80) can be reduced. Moreover, the accuracy of combination of the inner member (26) and the outer member (30) is improved. Further, the accuracy of combination of the protective cover (14) and the casing (16) is also improved.

In the third aspect of the present invention, the protective cover (14) further comprises an intermediate member (28) disposed between the inner member (26) and the outer member (30) and configured to cover the distal end portion (24) of the sensor element (12), and the intermediate member (28) is fitted to an inner surface of the outer member (30), and the inner member (26) is fitted to the inner surface of the outer member (30) and an inner surface of the intermediate member (28).

As a result, the above-described effects can be easily obtained.

In the third aspect of the present invention, the outer member (30), the intermediate member (28), and the inner member (26) are substantially coaxially fitted to each other.

As a result, the accuracy of combination of the components constituting the gas sensor (10, 80) and the measurement accuracy of the sensor element (12) are improved.

In the third aspect of the present invention, the outer member (30), the intermediate member (28) and the inner member (26) are fitted to each other by press fitting.

As a result, the above-described effects can be easily obtained.

Note that the present invention is not limited to the above disclosure, and various configurations can be adopted therein without departing from the gist of the present invention.

What is claimed is:

1. A method for manufacturing a gas sensor including a casing, a sensor element held by the casing, and a protective cover configured to protect a distal end portion of the sensor element that protrudes from the casing,
   wherein the protective cover includes an inner member disposed in the casing so as to surround the distal end portion of the sensor element, and an outer member disposed in the casing so as to cover the distal end portion of the sensor element and the inner member,
   the method comprising:
   forming the protective cover by fitting the inner member and the outer member to each other by press fitting; and
   connecting the outer member and a side surface of the casing to each other, connecting the inner member and the side surface of the casing to each other, and fixing by welding a connection portion between the outer member and the side surface of the casing, in a manner so that the distal end portion of the sensor element is covered with the protective cover, wherein
   a gas is introduced from outside into a space surrounded by the protective cover and the casing.

2. The method for manufacturing the gas sensor according to claim 1, wherein
   in the connecting of the casing and the protective cover, the protective cover and the casing are fitted to each other.

3. The method for manufacturing the gas sensor according to claim 2, wherein
   in the connecting of the casing and the protective cover, the protective cover and the casing are fitted to each other by press fitting.

4. The method for manufacturing the gas sensor according to claim 1, wherein
   the protective cover further includes an intermediate member disposed between the inner member and the outer member and configured to cover the distal end portion of the sensor element, and
   in the forming of the protective cover, the intermediate member is fitted to an inner surface of the outer member by press fitting, and thereafter, the inner member is fitted to the inner surface of the outer member and an inner surface of the intermediate member by press fitting.

5. The method for manufacturing the gas sensor according to claim 4, wherein
   the outer member, the intermediate member, and the inner member are substantially coaxially fitted to each other, and
   in the connecting of the casing and the protective cover, the casing and the protective cover are connected to each other in a manner so that the sensor element, the casing, and the protective cover are substantially coaxial with each other.

6. The method for manufacturing the gas sensor according to claim 1, wherein
   in the connecting of the casing and the protective cover, the connection portion between the outer member and the side surface of the casing is fixed by resistance welding.

7. The method for manufacturing the gas sensor according to claim 1, wherein
   in the connecting of the casing and the protective cover, the connection portion between the outer member and the side surface of the casing is fixed by laser welding.

8. The method for manufacturing the gas sensor according to claim 6, wherein
   in the connecting of the casing and the protective cover, the connection portion between the outer member and the side surface of the casing is fixed by spot welding.

9. A gas sensor comprising:
   a casing;
   a sensor element held by the casing; and
   a protective cover configured to protect a distal end portion of the sensor element that protrudes from the casing, wherein
   the protective cover includes an inner member disposed in the casing so as to surround the distal end portion of the sensor element, and an outer member disposed in the casing so as to cover the distal end portion of the sensor element and the inner member,
   the protective cover is formed by fitting the inner member and the outer member to each other by press fitting,
   the distal end portion of the sensor element is covered with the protective cover by connecting the outer member and a side surface of the casing to each other, connecting the inner member and the side surface of the casing to each other, and fixing by welding a connection portion between the outer member and the side surface of the casing, and
   a gas is introduced from outside into a space surrounded by the protective cover and the casing.

10. A protective cover that protects a distal end portion of a sensor element held by a casing, the protective cover comprising:

an inner member disposed in the casing so as to surround the distal end portion of the sensor element; and an outer member disposed in the casing so as to cover the distal end portion of the sensor element and the inner member, wherein the protective cover is formed by fitting the inner member and the outer member to each other by press fitting, the inner member and the outer member are connected by being fitted to each other, the outer member is connected to a side surface of the casing, the inner member is connected to the side surface of the casing, and a connection portion between the outer member and the side surface of the casing is fixed by welding.

11. The protective cover according to claim 10, further comprising an intermediate member disposed between the inner member and the outer member and configured to cover the distal end portion of the sensor element, wherein the intermediate member is fitted to an inner surface of the outer member, and the inner member is fitted to the inner surface of the outer member and an inner surface of the intermediate member.

12. The protective cover according to claim 11, wherein the outer member, the intermediate member, and the inner member are substantially coaxially fitted to each other.

13. The protective cover according to claim 11, wherein the outer member, the intermediate member, and the inner member are fitted to each other by press fitting.

\* \* \* \* \*